US011666613B2

(12) United States Patent
Liu et al.

(10) Patent No.: US 11,666,613 B2
(45) Date of Patent: Jun. 6, 2023

(54) USE OF LACTOBACILLUS PARACASEI SUBSP. PARACASEI K56 CAPABLE OF REGULATING GASTROINTESTINAL FLORA BALANCE

(71) Applicant: Inner Mongolia Yili Industrial Group Co., Ltd., Hohhot (CN)

(72) Inventors: Wei-Hsien Liu, Hohhot (CN); Wei-Lian Hung, Hohhot (CN); Ting Sun, Hohhot (CN); Wen Zhao, Hohhot (CN); Ignatius Man-Yau Szeto, Hohhot (CN)

(73) Assignee: Inner Mongolia Yili Industrial Group Co., Ltd., Inner Mongolia (CN)

( * ) Notice: Subject to any disclaimer, the term of this patent is extended or adjusted under 35 U.S.C. 154(b) by 0 days.

(21) Appl. No.: 17/135,266

(22) Filed: Dec. 28, 2020

(65) Prior Publication Data

US 2021/0113632 A1    Apr. 22, 2021

Related U.S. Application Data

(63) Continuation of application No. PCT/CN2019/107220, filed on Sep. 23, 2019.

(30) Foreign Application Priority Data

Sep. 30, 2018 (CN) .......................... 201811162941.X (51) Int. Cl.
*A61K 39/02* (2006.01)
*A61K 35/747* (2015.01)
*A23L 33/135* (2016.01)

(52) U.S. Cl.
CPC .......... *A61K 35/747* (2013.01); *A23L 33/135* (2016.08)

(58) Field of Classification Search
None
See application file for complete search history.

(56) References Cited

U.S. PATENT DOCUMENTS

| | | | | |
|---|---|---|---|---|
| 10,548,928 B2 * | 2/2020 | Grompone | ........... | A23C 9/1234 |
| 2011/0038837 A1 | 2/2011 | Nishida et al. | | |

FOREIGN PATENT DOCUMENTS

| | | | | |
|---|---|---|---|---|
| CN | 101357143 A | 2/2009 | | |
| CN | 101626774 A | 1/2010 | | |
| CN | 101768559 | 7/2010 | | |
| CN | 103243039 A | 8/2013 | | |
| CN | 104894021 A | 9/2015 | | |
| CN | 106604736 A | 4/2017 | | |
| CN | 107699528 A | 2/2018 | | |
| CN | 107916236 * | 4/2018 | ....... | A61K 2035/115 |
| CN | 107916236 A | 4/2018 | | |
| CN | 108315285 A | 7/2018 | | |
| CN | 108323761 A | 7/2018 | | |
| CN | 110882280 A | 3/2020 | | |
| CN | 110892940 A | 3/2020 | | |
| CN | 110892990 | 3/2020 | | |
| CN | 110903995 A | 3/2020 | | |
| EP | 1972208 A | 9/2008 | | |
| WO | 02053706 A1 | 7/2002 | | |
| WO | 2015159124 A1 | 10/2015 | | |
| WO | WO 2015/159240 * | 10/2015 | ............ | A61K 36/74 |
| WO | 2020/063515 A1 | 4/2020 | | |
| WO | 2020063531 A1 | 4/2020 | | |

OTHER PUBLICATIONS https://www.oed.com/view/Entry/247311?rskey=tleabF&result=1#eid; Old English Dictionary online current edition Sep. 2021.*
Wen, Z., et al., "In-Vitro and In-Vivo Evaluation of the Probiotic Potential of Lactobacillus paracasei Strain K56 For Modulating gastrointestinal Health", 10th Asian Conference on Lactic Acid Bacteria, Yogyakarta, Aug. 29-31, 2019 (Abstract Only).
Min, Q-Q., et al., "Differential Modulation of the Metabolic Effects of Diet-Induced Obesity by Probiotic Lactobacillus Paracasei K56 and Prebiotic α-Gaactooligosaccharides", Current Topics in Nutraceutical Research, 19(1): 21-28 (2021.
European Extended Search Report for EP Application No. 19864086.4, "Novel Use of Lactobacillus paracasei Subsp. paracasei K56 Capable of Regulating Gastrointestinal Flora Balance" dated May 17, 2021.
National Food Safety Standard Food Microbiological Test, Determination of Aerobic Plate Count, with English translation, No. GB 4789.2-2010; Mar. 26, 2010-June 1, 2010.
International Search Report issued in PCT/CN2019/107220, entitled "Novel Application of Lactobacillus Paracasei K56 Capable of Regulating Balance of Gastrointestinal Flora," dated Dec. 5, 2019.
Written Opinion issued in PCT/CN2019/107220, entitled "Novel Application of Lactobacillus Paracasei K56 Capable of Regulating Balance of Gastrointestinal Flora," dated Dec. 5, 2019.
International Preliminary Report on Patentability issued in PCT/CN2019/107220, entitled "Novel Application of Lactobacillus Paracasei K56 Capable of Regulating Balance of Gastrointestinal Flora," dated Mar. 23, 2021.
Lu, W., et al., Evaluation of Intestinal Microbiota in Mice after Oral Administration of Lactobacillus paracasei LCO1, Food Science, 37(23) 230-235 (2016).

(Continued)

*Primary Examiner* — Jennifer E Graser
(74) *Attorney, Agent, or Firm* — Hamilton, Brook, Smith & Reynolds, P.C.

(57) ABSTRACT

A new use of *Lactobacillus paracasei* subsp. *paracasei* K56 capable of regulating the gastrointestinal flora balance is described. The deposit number of the *Lactobacillus paracasei* subsp. *paracasei* is DSM27447. This strain alone has the ability to significantly promote the growth of intestinal *Bifidobacterium* and *Lactobacillus*, suppress *Desulfovibrio* and/or *Enterobacteria* in the intestine, suppress *Helicobacter* and/or *Escherichia-Shigella*, and can endure a simulated in vitro gastrointestinal fluid stress environment. Experiments in mice show that this strain has no acute oral toxicity, no antibiotic resistance, and may be safely used in food processing.

7 Claims, 3 Drawing Sheets

(56) References Cited

OTHER PUBLICATIONS

Bjerg, A.T., et al., "The effect of *Lactobacillus paracasei* subsp. *paracasei* L. casei W8® on blood levels of triacylglycerol is independent of colonization, Beneficial Microbes", 6(3), 7 pages (2014).

Canani R.B., et al., "Specific Signatures of the Gut Microbiota and Increased Levels of Butyrate in Children Treated With Fermented Cow's Milk Containing Heat-Killed Lactobacillus paracasei CA L74, Applied and Environmental Microbiology", Applied and Environmental Biology, 83(19), 10 pages (Oct. 2017).

Xiong, T., et al., Acid, Bile Tolerance and adhesion Properties of Lactobacillus paracasei NCU622, Food Science, 36(5), 93-98 (2015).

Ran, W., et al., "Effect of Lactobacillus casei L9 on Gut Health of Healthy Individuals", Journal of Chinese Institute of Food Science and Technology, 16(8), 7 pages (2016).

\* cited by examiner

USE OF *LACTOBACILLUS PARACASEI* SUBSP. *PARACASEI* K56 CAPABLE OF REGULATING GASTROINTESTINAL FLORA BALANCE

CROSS-REFERENCE TO RELATED APPLICATIONS

This application is a continuation of International Application No. PCT/CN2019/107220, filed on Sep. 23, 2019, which claims priority under 35 U.S.C. § 119 or 365 to Chinese Patent Application No. 201811162941.X, filed on Sep. 30, 2018, both of which are hereby incorporated by reference in their entireties.

TECHNICAL FIELD

The present invention relates to the technical field of microorganisms, in particular to a novel use of *Lactobacillus paracasei* subsp. *paracasei* K56 (Deposit number: DSM27447).

BACKGROUND

The balance of intestinal flora is closely related to human health. Intestinal flora includes beneficial bacteria, neutral bacteria and harmful bacteria. Beneficial bacteria prevail in the intestine of a healthy human and constantly interact with harmful bacteria to maintain health of the human body. If the beneficial bacteria in the intestine are reduced due to various factors, harmful bacteria will proliferate in a great number, breaking the microecological balance in the intestine, which causes enteritis, diarrhea, and other clinical symptoms. Further, antibiotics are usually used in a large amount clinically, and while effectively killing harmful bacteria, they also kill beneficial bacteria, causing intestinal flora imbalance and occurrence of diseases.

For those with imbalanced intestinal flora, oral supplementation of probiotics is a direct and effective way to regulate the intestinal flora. Oral supplementation of probiotic preparations or products containing probiotics can directly or indirectly adjust the composition of the intestinal flora, activate the host's endogenous microbiota or the activity of the immune system to achieve probiotic effects.

The World Health Organization defines a probiotic product as a food containing live microorganisms in a sufficient amount that can maintain an appropriate number of viable bacteria and bacterial activity even after being subjected to various processes in food processing and entering the human intestine. Therefore, it is necessary for a strain to be able to maintain a relatively stable number of viable bacteria after the bacterial powder is prepared and the product is produced and processed and withstands the gastric acid and bile salt stress in the human gastrointestinal tract. In addition, even though Lactobacilli are commonly recognized as safe strains, recent studies have shown that toxic factors and antibiotic resistance appeared in many *Lactobacilli*, especially food-borne *Lactobacilli* and intestinal *Lactobacilli*, which poses potential risks to human health. Therefore, in evaluating the probiotic characteristics of the strain, the safety of the strain during consumption and the stability during the production and processing thereof should also be taken into full consideration.

CN107916236A discloses a *Lactobacillus paracasei* subsp. *paracasei* K56, which was deposited in the German Collection of Microorganisms and Cell Cultures on Jun. 27, 2013, with the deposit number of DSM27447. CN107916236A also discloses the use of *Lactobacillus paracasei* subsp. *paracasei* K56 in regulating immune response, but provides no recordation or suggestion whether *Lactobacillus paracasei* subsp. *paracasei* K56 is effective in balancing the gastrointestinal flora.

SUMMARY

An object of the present invention is to provide a novel use of *Lactobacillus paracasei* subsp. *paracasei* K56.

A *Lactobacillus paracasei* sub sp. *paracasei* K56 strain has been deposited under the Budapest Treaty in the Leibniz Institute DSMZ-German Collection of Microorganisms and Cell Cultures, Inhoffenstr. 7 B, D-38124 Braunschweig, on Jun. 27, 2013, with the deposit number of DSM27447.

It is discovered in the present invention that the *Lactobacillus paracasei* subsp. *paracasei* K56 strain alone has the ability to significantly promote the growth of intestinal *Bifidobacterium* and *Lactobacillus*, inhibit *Desulphovibrio* and/or *Enterobacteria* in the intestine, and inhibit *Helicobacter* and/or *Escherichia-Shigella*, and can endure a simulated in vitro gastrointestinal fluid stress environment. Experiments in mice show that this strain has no acute oral toxicity, no antibiotic resistance, and may be safely used in food processing.

Thus, the present invention provides the use of *Lactobacillus paracasei* subsp. *paracasei* in the preparation of a composition for regulating gastrointestinal flora, the *Lactobacillus paracasei* subsp. *paracasei* having a deposit number of DSM27447.

According to a specific embodiment of the present invention, the *Lactobacillus paracasei* subsp. *paracasei* is used to prepare a composition in the form of a solid or liquid bacterial preparation.

According to a specific embodiment of the present invention, the composition may include a food composition, a feed composition, or a pharmaceutical composition.

According to a specific embodiment of the present invention, the composition may be used in animal or human. The composition may also include components conventionally used in the related field. For example, for a pharmaceutical composition, an appropriate amount of adjuvants may be included, and the adjuvants may be excipients, diluents, fillers, absorption enhancers and the like. For a food composition, *Bifidobacterium lactis* according to the present invention may be produced in line with a *Bifidobacterium lactis*-containing food in the prior art, and the composition can adopt different forms according to the needs of the recipient, for example, powder, lozenge, granulation, microcapsule, liquid preparation and the like.

According to a specific embodiment of the present invention, the composition is used to increase the amount of *Bifidobacterium* and/or *Lactobacillus* in the intestine. In a practical application, the amount of the *Lactobacillus paracasei* subsp. *paracasei* used is $1.0 \times 10^3$ CFU to $1.0 \times 10^{10}$ CFU/kg body weight/day, preferably $1.0 \times 10^4$ CFU to $1.0 \times 10^9$ CFU/kg body weight/day.

According to a specific embodiment of the present invention, the composition is used to suppress the amount of *Desulfovibrio* and/or *Enterobacter* in the intestine. In a practical application, the amount of the *Lactobacillus paracasei* subsp. *paracasei* used is $1.0 \times 10^3$ CFU to $1.0 \times 10^{10}$ CFU/kg body weight/day, preferably $1.0 \times 10^4$ CFU to $1.0 \times 10^9$ CFU/kg body weight/day.

According to a specific embodiment of the present invention, the composition is used to suppress the amount of *Helicobacter* and/or *Escherichia-Shigella*. In a practical application, the amount of the *Lactobacillus paracasei* subsp. *paracasei* used is $1.0 \times 10^3$ CFU to $1.0 \times 10^{10}$ CFU/kg body weight/day, preferably $1.0 \times 10^4$ CFU to $1.0 \times 10^9$ CFU/kg body weight/day.

In a specific embodiment of the present invention, the composition is a food composition, wherein the food is a fermented milk product (such as fermented milk, flavored fermented milk, fermented milk beverage and the like), cheese, a dairy beverage, a solid beverage or milk powder.

On the other hand, the present invention also provides a method of regulating gastrointestinal flora, the method comprising administering an effective amount of *Lactobacillus paracasei* subsp. *paracasei* to a subject, with the deposit number of the *Lactobacillus paracasei* subsp. *paracasei* being DSM27447.

According to a specific embodiment of the present invention, in the method of regulating gastrointestinal flora according to the present invention, the regulation of gastrointestinal flora includes increasing the amount of *Bifidobacterium* and/or *Lactobacillus* in the intestine, suppressing the amount of *Desulphovibrio* and/or *Enterobacteria* in the intestine, and/or suppressing the amount of *Helicobacter* and/or *Escherichia-Shigella*.

According to a specific embodiment of the present invention, in the method of regulating gastrointestinal flora according to the present invention, the *Lactobacillus paracasei* subsp. *paracasei* is administered in an amount of $1.0 \times 10^3$ CFU to $1.0 \times 10^{10}$ CFU/kg body weight/day to the subject. In some further specific embodiments, the *Lactobacillus paracasei* subsp. *paracasei* is administered in an amount of $1.0 \times 10^4$ CFU to $1.0 \times 10^9$ CFU/kg body weight/day to the subject.

In summary, the present invention provides a new use of *Lactobacillus paracasei* subsp. *paracasei* K56, and this bacterium is effective in regulating gastrointestinal flora, in particular, suppressing *Desulfovibrio* and/or *Enterobacter* in the intestine and suppressing *Helicobacter* and/or *Escherichia-Shigella*, and can be used to prepare foods, medicines and feeds for regulating intestinal flora, which has a broad prospect in application.

DESCRIPTION OF EMBODIMENTS

For better understanding of the technical features, the purpose, and advantageous effects of the present invention, the technical solutions of the present invention are now described in detail in connection with specific examples. It should be understood that these examples are only used to illustrate the present invention, but not to limit the scope of the present invention. In the examples, the starting reagents and materials are commercially available, and the experimental methods without specified conditions are conventional methods and conventional conditions well known in the art, or in accordance with the conditions recommended by the instrument manufacturer.

Unless specifically defined otherwise, all technical and scientific terms used herein have the same meaning as those of ordinary skill in the relevant art commonly understand. Unless otherwise specified, all numbers used in the present invention indicating the amounts of ingredients, cell culture, treatment conditions and the like should be understood as being modified by the term "about" under all circumstances. Therefore, unless otherwise stated, the numerical parameters are approximate values and may vary according to the desirable characteristics intended to be obtained by the present invention. Unless otherwise stated, the term "at least" preceding a series of elements should be understood to refer to each element in the series.

In each example of the present invention, unless otherwise specified, the experimental data is expressed as Mean±S.E.M. The data is calculated by PRISM version 5.0 (GraphPad, San Diego, Calif., USA). Differences between groups are calculated by one-way ANOVA followed by Tukery's multiple comparison test. A significant statistical difference is present at $P<0.05$.

EXAMPLE 1: GASTRIC ACID RESISTANCE TEST

The MRS culture medium was adjusted to pH 2.0, pH 2.5, and pH 3.0 respectively with a 0.1N HCl solution, and 100 μL (109 CFU/ml) of the activated bacteria solution was inoculated in 10 mL of test solutions at different pH. The viable bacteria having an initial concentration of approximately 107 CFU/mL was placed at 37° C. for 1 hour and sampled to measure the number of the remaining bacteria. 1 mL of the bacteria solution was taken, serially diluted with a 0.85% saline solution, applied on MRS agar, and incubated at 37° C. for 24 to 48 hours to calculate the number of colonies generated. In addition, 100 μL of a *Lactobacillus* solution (109 CFU/ml) was added to an MRS culture medium without pH adjustment (pH 6.8) as control.

The acid resistance of the strain (%)=(the number of remaining bacteria in the test solution at pH 2.0 (or pH 2.5 or pH 3.0)/the number of bacteria in the MRS culture solution without pH adjustment)×100%

Acid resistance is considered as one of the necessary characteristics for Lactobacillus to survive in the acidic environment in the stomach. The results of the acid resistance of K56 in different acidic environments are shown in Table 1 below. The results show that the number of the initial viable bacteria was $2.96 \times 10^7$ CFU/mL. After 1 hour in an acidic environment, the strain K56 survived in the tolerant conditions of pH 2.5 and pH 3.0, though it was almost completely killed after 1 hour of pH 2.0 treatment (0%). The survival rate was 6.39% at pH 2.5, and the strain was less sensitive to an acidic environment at pH 3 and maintained a survival rate of 84.31%.

TABLE 1

K56 acid resistance test results

| Strain | Number of bacteria in control (CFU/mL) MRS (pH6.8) | Survival rate under different acidic environments (%) | | |
|---|---|---|---|---|
| | | pH2.0 | pH2.5 | pH3.0 |
| K56 | 2.96E+07 | 0.00% | 6.39% | 84.31% |

EXAMPLE 2. BILE SALT RESISTASNCE TEST

MRS culture media containing test solutions having oxgall bile at different concentrations of 0.1%, 0.5% and 1%, respectively, were prepared. 100 μL (109 CFU/ml) of activated bacteria solution was taken and inoculated in 10 mL of the test solutions containing oxgall bile at different concentrations. The viable bacteria having an initial concentration of about 107 CFU/mL was placed at 37° C. for 1 hour and sampled to measure the number of the remaining bacteria. 1 mL of the bacteria solution was taken, serially diluted with PBS (0.1 M, pH 6.2), applied on MRS agar, incubated at 37° C. for 24 to 48 hours to calculate the number of colonies generated. In addition, 100 μL of a *Lactobacillus* solution (109 CFU/ml) was added to an MRS culture medium (pH 6.8) without oxgall bile as control.

Bile salt resistance of the strain (%)=(the number of remaining bacteria in the test solution containing 0.1% (or 0.5% or 1%) oxgall bile/the number of bacteria in the test solution without oxgall bile)×100%

Bile salt resistance is considered as one of the necessary characteristics for *Lactobacillus* to survive in the small bowel. The results of the resistance of the strain K56 to different concentrations of bile salt for 1 hour are shown in Table 2. It can be seen that as the bile salt concentration increases, the sensitivity of the strain to the bile salt increases, which results in the increase in the mortality rate. the initial number of viable bacteria was 4.34×107 CFU/mL, and the strain K56 had 89.60% resistance to 0.1% bile salt after 1 hour incubation, 82.73% resistance to 0.5% bile salt after 1 hour incubation, and a 69.44% survival rate at 1% bile salt concentration. In summary, it shows that K56 is highly resistant to an acidic environment and a bile salt-containing environment.

TABLE 2

K56 bile salt resistance test results

| Strain | Number of bacteria in control (CFU/mL) | Survival rate under environments with oxgall bile at different concentrations (%) | | |
|---|---|---|---|---|
| | MRS | 0.1% Oxgall | 0.5% Oxgall | 1% Oxgall |
| K56 | 4.34E+07 | 89.60% | 82.73% | 69.44% |

EXAMPLE 3: INTESTINAL CELL ADHESION EFFECT

Caco-2 cells were cultured in a culture flask. A DMEM cell culture medium containing 10% heat-inactivated fetal bovine serum and double antibiotics (100 U/mL penicillin and 100 μg/mL streptomycin) was added into the flask and placed and cultured in an incubator at 37° C., 5% CO2, with the culture medium changed every 2 days. After the cells grew into an adhering single cell layer (5 to 7 days), they were digested and passaged with 0.25% trypsin, and stained with a 0.4% trypan blue staining solution. A hemocytometer was used to determine the number and activity of the cells under a microscope in order to ensure a cell activity of above 95%.

Figure 1A:
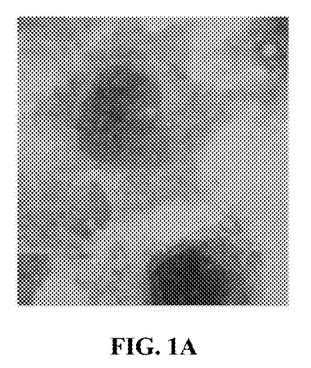
FIG. 1A and FIG. 1B show a schematic microscopic photograph of intestinal adhesion of *Lactobacillus paracasei* subsp. *paracasei* K56.
Figure 1B:
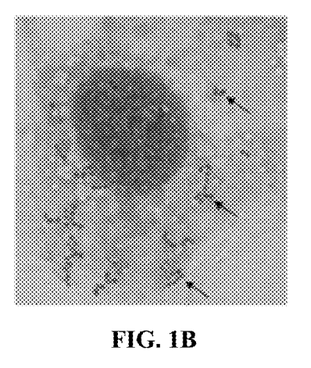
Figure 2:
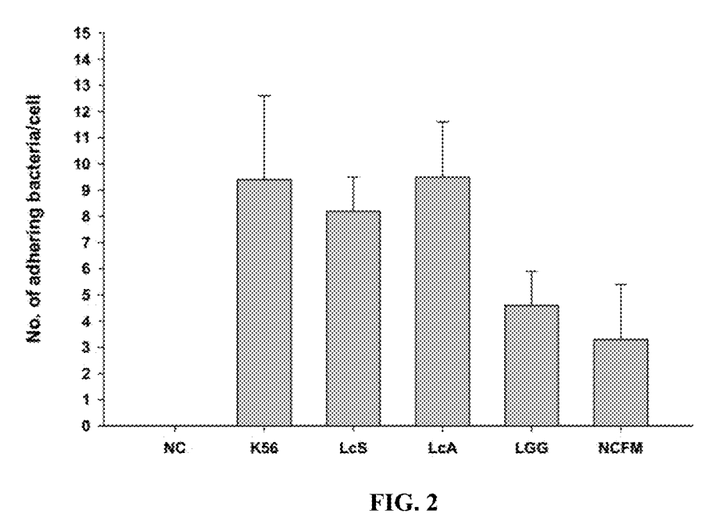
FIG. 2 shows the results of the intestinal adhesion comparison test of *Lactobacillus paracasei* subsp. *paracasei* K56.

The adhesion of the strain to Caco-2 cells was tested in an adhesion experiment. The results are shown in FIG. 1 (panel B is an enlarged view of panel A). FIG. 2 shows that K56 has an intestinal adhesion ability similar to LcS and LcA and better than LGG and NCFM.

EXAMPLE 4: INTESTINAL FLORA REGULATION EFFECT

In this example, it is intended to verify the effect of *Lactobacillus paracasei* subsp. *paracasei* according to the present invention in intestinal regulation. Reference can be made to "Technical Specifications for Health Food Examination and Evaluation: Standards for Intestinal Flora Function Regulation" for the principles and procedures.

Forty-two healthy SPF BABL/c mice weighing 18-22 g (supplied by Beijing Huafukang Biotechnology Co., Ltd.) were taken. After 3 days of adaptive feeding, they were randomly divided into 3 groups, each with 14 animals, i.e., a blank control group and a sample group. Each group of animals was gavaged with sterile water having dissolved *Bifidobacterium lactis* K56 powder (gavage volume 0.2 mL/10 g), and the blank control group was gavaged with sterile water of the same volume. The feeding or gavage was done once a day for 14 days consecutively. Gavage volume: $1.3 \times 10^7$ CFU/ml (converted in accordance with an amount of $2 \times 10^9$ CFU/d as needed by human, with a conversion factor between human and mouse of 0.0026). After the adaptive feeding, mouse feces was collected under aseptic conditions into numbered sterile centrifuge tubes, with 2-3 pellets of about 100 mg from each mouse, and transferred to an aseptic operation room under low temperature conditions for flora measurement. At the end of the experiment, mouse feces were collected again. The mice were grouped and numbered with picric acid, weighed on the 8th and 14th days of administration of the test substance, and the gavage volume of the mice was calculated. The mice were weighed once at the end of the experiment. Colony counting: selective media were prepared according to the strain to be identified. The strain to be tested and the corresponding medium are shown in Table 3. Sterilization was carried out followed by uniform shaking, cooling to 45° C.-50° C., and pouring into a plate before use.

TABLE 3

Test strains and corresponding selective medium

| Strains to be tested | Selective medium |
|---|---|
| *Enterobacter* | Eosin Methylene Blue (EMB) Agar |
| *Enterococcus* | Sodium Azide-Crystal Violet-Aescin Agar |
| *Bifidobacterium* | BBL Agar |
| *Lactobacillus* | LBS Agar |
| *Clostridium perfringens* | Tryptone-Sulfite-Cycloserine (TSC) Agar |

The collected mouse feces were placed in a sterile tube containing 0.5 mL of normal saline, prepared into a bacterial suspension, and shaken for 1 min before use. 0.1 mL of the bacteria suspension was taken with a 0.1 mL micropipette, slowly injected into 0.9 mL of sterile saline, shaken or repeatedly pipetted to mix well to make a 1:10 bacteria suspension. A 10-fold gradient dilution was conducted in the same way to 10 to 7 g/ml by using another 0.1 mL micropipette tip. According to the number of viable bacteria to be identified, two consecutive appropriate dilutions were selected. For each dilution, 10 μL of bacterial suspension was taken by a 10 μL micropipette, surface coated on a plate with the selective agar, and cultured according to the culture conditions shown in Table 2. For the colony counting method, reference can be made to "GB 4789.2-2010 National Food Safety Standard, Food Microbiological Examination: Aerobic Plate Count".

TABLE 4

Intestinal flora test medium and identification method

| Items | Medium | Culture condition |
|---|---|---|
| Enterobacter | Eosin Methylene Blue Agar | 24 h culture, 36° C. ± 1° C. |
| Enterococcus | Sodium Azide-Crystal Violet-Aescin Agar | 48 h culture, 36° C. ± 1° C. |
| Bifidobacterium | BBL Agar | 48 h anaerobic culture, 36° C. ± 1° C. |
| Lactobacillus | LBs Agar | 48 h culture, 36° C. ± 1° C. |
| Clostridium perfringens | TSC Agar | 24 h anaerobic culture, 36° C. ± 1° C. |

SPSS17.0 was used for data statistics. The changes of *Bifidobacterium, Lactobacillus, Enterococcus*, and *Enterobacteria* before and after the experiment and between the groups were compared. For the test group, the change before and after the experiment was significant, and the animal test result of the test sample could be determined as positive if any of the following conditions was met: (i) there was a significant increase in *Bifidobacterium* or *Lactobacillus* in feces, a decrease or no significant change in *Clostridium*, no significant change in *Enterococcus* or *Enterobacter*; (ii) there was a significant increase in *Bifidobacterium* or *Lactobacillus* in feces, a decrease or no significant change in *Clostridium*, and a significant increase in *Enterococcus* and *Enterobacter* with the increase being lower than the increase in *Bifidobacterium* or *Lactobacillus*.

Figure 3:
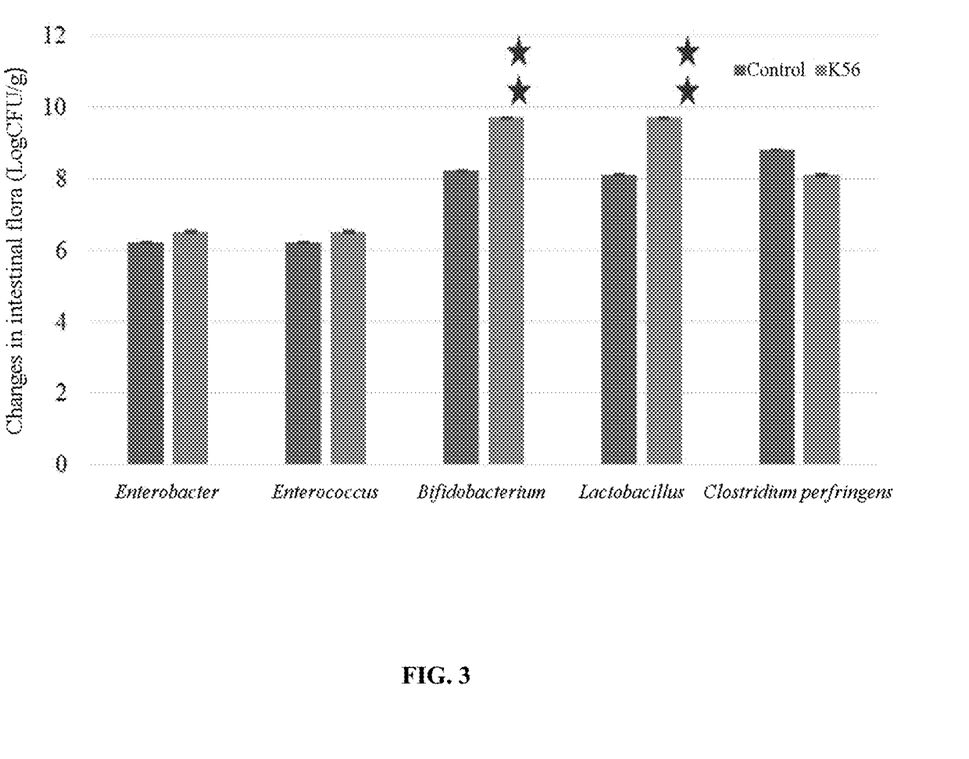
FIG. 3 shows the test results of *Lactobacillus paracasei* subsp. *paracasei* K56 in regulating intestinal flora.

The results of the body weight changes of animals during the experiment are shown in Table 5. During the experiment, the animals showed normal characteristics, and no adverse reaction occurred after the administration of the test substance. Over the experiment period, there was no significant difference in body weight between the two groups of animals. From Table 6 to Table 10, it can be seen that *Lactobacillus paracasei* subsp. *paracasei* K56 can significantly promote the growth of *Bifidobacterium* and *Lactobacillus*, while having no significant effect on *Enterobacter, Enterococcus*, and *Clostridium perfringens*. According to the "Technical Specifications for Health Food Examination and Evaluation: Standards for Intestinal Flora Function Regulation", it can be concluded that the *Lactobacillus paracasei* subsp. *paracasei* K56 in this study has the effect of regulating intestinal flora (See FIG. 3).

TABLE 5

Animal body weight changes

| Group | Number of animals | Initial weight (g) | Mid-term weight (g) | Final weight (g) |
|---|---|---|---|---|
| Control | 14 | 21.89 ± 1.25 | 22.14 ± 0.87 | 21.24 ± 0.87 |
| K56 | 14 | 22.11 ± 1.08 | 21.79 ± 1.17 | 20.95 ± 0.22 |

TABLE 6

Changes in animal intestinal *Bifidobacterium* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 8.66 ± 0.57 | 8.94 ± 0.46 | 0.196 | |
| K56 | 14 | 8.87 ± 0.59 | 9.80 ± 0.63** | 0.009 | 0.002 |

TABLE 7

Changes in animal intestinal *Lactobacillus* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 8.54 ± 0.57 | 8.45 ± 0.18 | 0.566 | |
| K56 | 14 | 8.76 ± 0.56 | 9.72 ± 0.57** | 0.000 | 0.000 |

TABLE 8

Changes in animal intestinal *Enterobacter* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 6.48 ± 0.32 | 6.98 ± 0.74 | 0.123 | |
| K56 | 14 | 7.00 ± 0.38 | 7.30 ± 0.13 | 0.001** | 0.055 |

TABLE 9

Changes of animal intestinal *Enterococcus* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 6.62 ± 0.27 | 6.78 ± 0.61 | 0.467 | |
| K56 | 14 | 6.97 ± 0.30 | 7.21 ± 0.41 | 0.058 | 0.052 |

TABLE 10

Changes in animal intestinal *Clostridium perfringens* before and after the test (LgCFU/g)

| Group | Number of animals | Before intervention | After intervention | p value for in-group comparison before and after intervention | p value for comparison with control after intervention |
|---|---|---|---|---|---|
| Control | 14 | 8.71 ± 0.17 | 9.10 ± 0.49 | 0.060 | |
| K56 | 14 | 8.60 ± 0.43 | 8.74 ± 0.57 | 0.465 | 0.091 |

EXAMPLE 5: COMPARISON OF THE INTESTINAL FLORA REGULATING EFFECTS OF K56 AT DIFFERENT DOSES

In this example, the intestinal flora regulating effect of K56 at different doses was tested.

Viable bacteria sample: according to the sample specification, 1 g of K56 viable bacteria sample was weighted and suspended in a PBS solution to 40 ml; namely, the concentration of the viable bacteria was $2.5 \times 10^9$ CFU/ml.

High-dose group: the gavage dose for a 20 g mouse was 0.4 ml as calculated according to a gavage amount of 0.2 ml/10 g in mice, and the gavage dose for the mice in the high-dose group was $10^9$ CFU/20 g.

Medium-dose group: 5 ml of the high-dose suspension was taken and added to PBS to a volume of 50 ml; the gavage dose for a 20 g mouse was 0.4 ml as calculated according to a gavage amount of 0.2 ml/10 g in mice, and the gavage dose for the mice in the medium-dose group was $10^8$ CFU/20 g.

Low-dose group: 5 ml of the medium-dose suspension was taken and added to PBS to a volume of 50 ml; the gavage dose for a 20 g mouse was 0.4 ml as calculated according to a gavage amount of 0.2 ml/10 g in mice, and the gavage dose for the mice in the low-dose group was $10^7$ CFU/20 g.

Six-week-old BABL/c mice were raised in a clean grade animal housing at a temperature of 22° C. and humidity of 10-60%, with 12 hour-lighting alternating between light and darkness, and provided with standard feed and free drinking water. The mice was adaptively fed for 5 days and randomly divided into groups with 14 mice in each group. The groups are shown in Table 11.

TABLE 11

Groups in the experiment of intestinal flora regulation

| Groups | Test substance | Number of animals | Gavage amount (Calculated as CFU/d in terms of daily intake by human) |
|---|---|---|---|
| Control | PBS | 14 | — |
| Low-dose | PBS + K56 | 14 | $3.88 \times 10^9$ |
| Medium-dose | PBS + K56 | 14 | $3.88 \times 10^{10}$ |
| High-dose | PBS + K56 | 14 | $3.88 \times 10^{11}$ |

Before the gavage, the feces of each mouse was collected under aseptic conditions, labeled, and stored at −20° C., and the intestinal flora was examined. In the experiment, each test substance was administered according to a gavage amount of 0.2 ml/10 g, and PBS was given to the control group on Day 1 to Day 14. The experimental groups were given the corresponding dose of test substance by gavage according to Table 11. The mice were weighed once a week, and the gavage volume was adjusted according to the body weight. After 14 days, the feces of each mouse were collected under aseptic conditions, labeled, and stored at −20° C., and the intestinal flora was examined.

Before and after the experiment, there was no significant difference in body weight among the mice in each group. At the phylum level, after supplementing of different doses of probiotics, the relative abundance of *Firmicutes* in the mouse intestinal flora increased while the relative abundance of *Bacteroidetes* and *Proteobacteria* decreased. Studies have shown that the ratio of *Firmicutes* to *Bacteroides* was closely correlated with intestinal diseases in human, and patients with obesity tend to have a lower ratio. However, patients with enteritis and intestinal stress syndrome tend to have a higher abundance of *Proteobacteria*.

The effect of K56 on the intestinal flora at the genus level is shown in Table 12.

TABLE 12

The effect of K56 on the intestinal flora

| Genus | Control | Low-dose | Medium-dose | High-dose |
|---|---|---|---|---|
| Bacteroides | 9.8061 ± 2.094 | 6.0503 ± 1.6172 | 7.4157 ± 2.3149 | 6.5026 ± 1.553 |
| Lactobacillus | 3.0166 ± 0.4635 | 0.5798 ± 0.5605 | 4.0343 ± 0.5534 | 2.158 ± 1.2288 |
| Desulfovibrio | 2.1391 ± 0.5097 | 0.853 ± 0.3645 | 1.5655 ± 0.9228 | 0.8367 ± 0.4632 |
| Enterobacter | 0.3447 ± 0.0971 | 0.254 ± 0.1668 | 0.2834 ± 0.1117 | 0.2134 ± 0.0873 |

At the genus level, in the probiotic family of the intestinal flora, the K56 medium-dose group can significantly increase the relative abundance of Lactobacillus in the mouse intestine as compared to the control group. The K56 low-dose group and high-dose group have a significant suppressive effect on Desulfovibrio.

The inhibitory effect of K56 on the pathogenic bacteria Helicobacter and Escherichia-Shigella is shown in Table 13.

TABLE 13

The inhibitory effect of K56 on pathogenic bacteria

| Genus | Control | Low-dose | Medium-dose | High-dose |
|---|---|---|---|---|
| Helicobacter | 0.1254 ± 0.0492 | 0.059 ± 0.028 | 0.0978 ± 0.0468 | 0.0459 ± 0.0325 |
| Escherichia-Shigella | 0.0281 ± 0.0054 | 0.0104 ± 0.0061 | 0.0236 ± 0.0061 | 0.0027 ± 0.0031 |

The results of the analysis of pathogenic bacteria show that the K56 low-dose group had a significant inhibitory effect on *Escherichia-Shigella*, and all the groups have a significant inhibitory effect on *Helicobacter*.

The above experiments demonstrate that K56 can regulate the intestinal flora balance, promote the growth of beneficial bacteria, and inhibit harmful bacteria and even pathogenic bacteria.

What is claimed:

1. A method for regulating gastrointestinal flora, comprising administering a composition comprising *Lactobacillus paracasei* subsp. *paracasei* to a subject, wherein the deposit number of the *Lactobacillus paracasei* subsp. *paracasei* is DSM27447, wherein the composition increases the amount of *Bifidobacterium, Lactobacillus* or both in the intestine, and suppresses the amount of *Desulfovibrio, Enterobacter* or both in the intestine, and suppresses the amount of *Helicobacter, Escherichia-Shigella* or both, and wherein the amount of the *Lactobacillus paracasei* subsp. *paracasei* present in the composition is $1.0 \times 10^3$ CFU to $5.0 \times 10^8$ CFU/kg body weight/day.

2. The method according to claim 1, wherein the composition is in the form of a solid or liquid bacterial preparation.

3. The method according to claim 1, wherein the composition includes a food composition, a feed composition, or a pharmaceutical composition.

4. The method according to claim 1, wherein the composition is a food composition, and wherein the food is a fermented dairy product, cheese, a dairy beverage, a solid beverage, or milk powder.

5. A method for regulating gastrointestinal flora, comprising administering an effective amount of *Lactobacillus paracasei* subsp. *paracasei* to a subject, wherein the deposit number of the *Lactobacillus paracasei* subsp. *paracasei* is DSM27447, wherein the *Lactobacillus paracasei* subsp. *paracasei* increases the amount of *Bifidobacterium, Lactobacillus* or both in the intestine, and suppresses the amount of *Desulfovibrio, Enterobacter* or both in the intestine, and suppresses the amount of *Helicobacter, Escherichia-Shigella* or both, and wherein the *Lactobacillus paracasei* subsp. *paracasei* is administered to the subject in an amount of $1.0 \times 10^3$ CFU to $5.0 \times 10^8$ CFU/kg body weight/day.

6. The method according to claim 5, wherein the *Lactobacillus paracasei* subsp. *paracasei* is administered to the subject in an amount of $1.0 \times 10^4$ CFU to $5.0 \times 10^8$ CFU/kg body weight/day.

7. The method of claim 1, wherein the amount is $1.0 \times 10^4$ CFU to $5.0 \times 10^8$ CFU/kg body weight/day.

* * * * *